United States Patent [19]
Sosebee

[11] Patent Number: 5,988,172
[45] Date of Patent: Nov. 23, 1999

[54] PERINEAL SURGICAL APRON

[76] Inventor: Shirley G. Sosebee, P.O. Box 437, Dawsonville, Ga. 30534

[*] Notice: This patent is subject to a terminal disclaimer.

[21] Appl. No.: 09/166,048

[22] Filed: Oct. 5, 1998

Related U.S. Application Data

[63] Continuation of application No. 08/953,137, Oct. 17, 1997, Pat. No. 5,816,253.

[51] Int. Cl.$^6$ ................................................. A61B 19/00
[52] U.S. Cl. ........................................... 128/849; 128/852
[58] Field of Search .................................... 128/849–856

[56] References Cited

U.S. PATENT DOCUMENTS

| | | |
|---|---|---|
| Re. 27,710 | 7/1973 | Melges ........................................ 128/853 |
| 1,491,011 | 4/1924 | Hodgin . |
| 3,030,957 | 4/1962 | Melges ........................................ 128/853 |
| 3,494,356 | 2/1970 | Melges ........................................ 128/132 |
| 3,503,391 | 3/1970 | Melges ........................................ 128/853 |
| 3,791,382 | 2/1974 | Collins ........................................ 128/853 |
| 3,921,627 | 11/1975 | Wilson ........................................ 128/853 |
| 4,471,769 | 9/1984 | Lockhart ..................................... 128/849 |
| 4,476,860 | 10/1984 | Collins ........................................ 128/853 |
| 4,570,628 | 2/1986 | Neal ........................................... 128/853 |
| 4,690,137 | 9/1987 | Starzmann ............................... 128/132 D |
| 4,903,710 | 2/1990 | Jessamine et al. ......................... 128/849 |
| 4,974,604 | 12/1990 | Morris ......................................... 128/853 |
| 5,388,593 | 2/1995 | Thomalla .................................... 128/849 |
| 5,522,403 | 6/1996 | Bark ............................................ 128/849 |

Primary Examiner—Michael A. Brown
Attorney, Agent, or Firm—Kennedy, Davis & Hodge

[57] ABSTRACT

A perineal surgical apron (10) for use in obstetrics and surgical procedures which apron comprises a fluid impermeable drape (11) having adhesive strips (15) and (15') at distal ends, and ties (17) for attaching the drape to a covering over a patient and to garb worn by the doctor and thereby defining a surgical surface between the doctor and the patient. An absorbent pad (24) centrally attached to the drape absorbs fluid from the surgical instruments used during surgical procedures. Side pockets (20) on the drape capture surgical instruments which are dropped or fall from the grasp of the doctor. Additional pockets (26) and (28) attached to the drape hold instruments for use during surgical procedures.

24 Claims, 3 Drawing Sheets

PERINEAL SURGICAL APRON

This application is a continuation of application Ser. No. 08/953,137, filed Oct. 17, 1997, now U.S. Pat. No. 5,816,253.

TECHNICAL FIELD

The present invention relates to surgical aprons for use by doctors when operating on or examining the perineal regions of patients, while the patients are in a lithotomy position on surgical tables.

BACKGROUND OF THE INVENTION

Gynecological and general surgical procedures are often performed on patients by doctors who sit adjacent and between the legs of the patients. While this close proximity facilitates performing the examinations and procedures, this position also presents logistical problems for doctors. The problems include storage and retrieval of both clean and used surgical instruments as well as maintaining sterile operating surfaces. Typically, doctors use scrub nurses to pass instruments and sutures from a back table during these types of surgical procedures. The doctor must therefore either hold out their outstretched arm to receive an instrument or turn from the site to face the scrub nurse to receive the instrument. If a scrub nurse is not available, the doctor must physically turn and in some instances stand to reach an instrument. The instruments must be placed in collection bins after use. Furthermore, these types of medical procedures often release fluids from a patient, which, because of the doctor's location, can be communicated to the doctor. These fluids include bodily fluids and blood released by the patient as well as irrigation and injection fluids used during the procedure. The current garments worn by doctors during these types of procedures do not offer complete protection from contamination by these fluids. The fluids also make the surgical instruments slippery, and therefore difficult to handle. In the event a surgical instrument falls to the floor, the instrument cannot be re-used in that procedure without cleaning and sterilization.

Patient drapes have been developed to address these problems of surgical procedures. For instance, disposable obstetrical abdominal drapes have been developed to aid physicians during surgical and examination procedures performed on the genital regions of patients. One type of drape overlies the abdominal and thoracic portions of patients during surgery. These drapes maintain the surgical instruments in close proximity to the patient and surgeon. For instance, such surgical drapes are disclosed in U.S. Pat. Nos. Re. 27,710 and 4,476,860 to Melges and Collins respectively. Such drapes typically are tailored to provide coverage of patients during procedures while maintaining sterile environments around the patients. In addition, such drapes provide liquid barriers that prevent fluids from passing through the drapes to the patients or to the doctors and prevent the saturation of surgical drapes during procedures.

These drapes however are not practical for perineal procedures. The abdominal and thoracic drapes include openings appropriate for such surgeries. Further, the doctor typically stands during such surgeries lateral of the patient. The pockets accordingly are lateral of the drape in close proximity to the doctor. In contrast, with the patient in the lithotomy position, the doctor sits between the legs of the patient for perineal surgeries. Abdominal and thoracic drapes would not provide satisfactory protection from contamination of instruments which fall from the hands of the doctor. Further, such drapes used for perineal surgeries would unsatisfactorily provide work surfaces convenient to the doctor, and the doctor would be continually standing up to obtain instruments and store them.

The inventor of the present invention previously developed a drape for perineal surgeries. The drape creates a continuous sterile surface between a physician and a patient undergoing perineal procedures. The surgical drape includes draw strings on one of its sides for attachment of the drape around the waist of the physician. Clips attach the opposing edge of the drape to the drape on the patient. The drape defines a trough-shaped surgical surface. Doctors using the drape can control the shape of the surface and the distance between themselves and their patients by moving a seat such as a rollable stool towards or away from the patient. A side pocket is formed along each of the side edges. The side pockets are to receive a surgical instrument, should one fall from the hands of the doctor during a procedure.

While the drape provides a sterile environment during perineal procedures, the drape still suffers from several disadvantages. It has been found that instruments which slip from the hand of the doctor during procedures are not caught satisfactorily in the side pockets. The elongate, flexible nature of the pockets allow the instrument to often slide out and fall to the floor. Such fallen instruments cannot be re-used in the procedure without breaching the sterile field. Further, while providing a trough-like surface of protection between a patient and doctor, the surgical drape does not provide a work space appropriate for surgical procedures for conducting the operation. Particularly, the drape is not able to assuredly isolate used surgical instruments or fluids. The impermeable sheet defining the surgical drape does not allow for absorption of excess fluids typically released during perineal procedures. The surgical drape also uses clips for fastening the drape to the garments covering the patient. The clips may slippingly release engagement, and the surgical trough at least partially collapses.

It thus is seen that a need remains for a surgical drape which provides a sterile surgical operating surface conveniently disposed between a patient and a doctor which drape provides pockets for holding surgical instruments while more reliably receiving dropped instruments and absorbing fluids therefrom for subsequent continued use during surgical procedures. It is to such that the present invention is directed.

SUMMARY OF THE INVENTION

The present invention meets the needs of the art by providing a perineal surgical apron for use in obstetrics and surgical procedures. The apron provides a fluid impermeable sheet-like drape, having an upper surface and a lower surface. The drape defines a patient edge and an opposing doctor edge, and two opposing side edges. An adhesive strip is attached on the patient edge for connecting the edge of the drape to a covering on the patient. A second adhesive strip secures the doctor edge of the drape to the medical garb worn by the doctor. The drape also includes a fabric strip on the doctor's edge having free distal ends for tying the drape around the waist of the doctor using the drape.

In a first embodiment, an absorbent pad attaches to a central portion of the upper surface and defines a receiving area on the drape for absorbing fluids from surgical instruments used during the surgical procedures.

In a second embodiment, at least two side pockets are defined on portions of the drape near each opposing side edge. The pockets open towards the opposing side edge, for receiving instruments that drop to the drape during the surgical procedure. The side pockets on each side are coaxially aligned and separated by a connector which attaches the pockets to the drape intermediate the opposing patient and doctor edges of the drape.

In a third embodiment, a plurality of open-ended instrument pockets are attached to a portion of the upper surface of the drape near the patient edge, for holding instruments for use during the surgical procedure. The openings of the instrument pockets face the patient.

Other objects, features and advantages of the present invention will become apparent upon reading the following detailed description of the disclosed embodiment of the present invention, in conjunction with the appended drawings and claims.

DETAILED DESCRIPTION OF THE INVENTION

Figure 1:
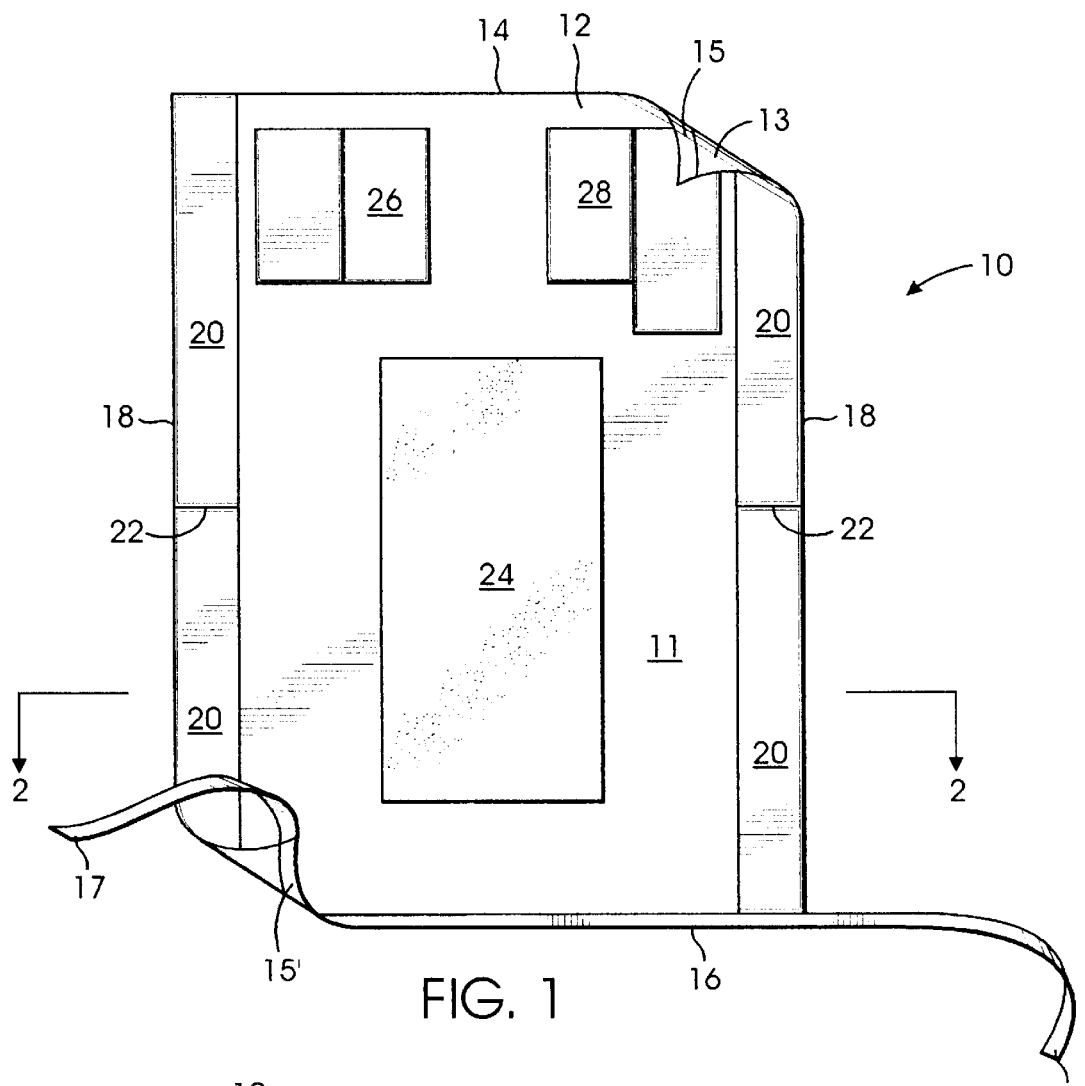
FIG. 1 is a top view of a preferred embodiment of a perineal surgical apron according to the present invention.

With reference to the drawings, in which like numerals refer to like parts, FIG. 1 illustrates a top view of a perineal surgical apron 10 according to the present invention, for use in gynecological and general examinations and surgical procedures. The perineal surgical apron 10 comprises a rectangular sheet-like drape 11 having an upper surface 12 and a lower surface 13. The drape 11 defines a patient edge 14 and an opposing doctor edge 16 and a pair of opposing side edges 18. The drape 11 is preferably made of a fluid-impermeable material. Double-sided adhesive tape strips 15 and 15' are positioned on the lower surface 13 of the drape 11, along the patient and doctor edges 14, 16, respectively. A first adhesive side secures the tapes 15 and 15' to the drape 11. A second adhesive side of the tapes 15 and 15' includes a tear-away covering, for use during a surgical procedure as discussed below. A flexible fabric strip 17 attaches to the doctor edge 16 of the drape 11 and extends laterally from the opposing side edges 18.

Figure 2:
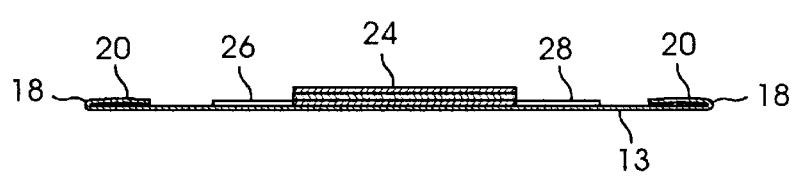
FIG. 2 is a cross-sectional view of the perineal surgical apron shown in FIG. 1 taken along line 2—2.

The side portions of the drape 11 adjacent the opposing edges 18 have a pair of side pockets 20. Each of the side pockets 20 are separated by a connector seam 22 located intermediate the patient edge 14 and the doctor edge 16. As best illustrated in FIG. 2, which shows a cross-sectional view of the apron of FIG. 1 along line 2—2, the opposing side pockets 20 open towards the pockets 20 on the opposite side. The pockets 20 are preferably defined by folding a portion of the side of the drape 11 over the drape itself, so that the upper surface 12 of the portion faces the upper surface 12 of the drape 11 adjacent to that portion. The edges of the folded portions are attached to the drape by sewing seams along the patient and doctor edges 14, 16, and by sewing the intermediate seam 22. Alternatively the seams can be created by adhesive or heat sealing techniques. It should be appreciated that the opposing side pockets can also be separate pockets formed of sheet materials, which are affixed to the upper surface 12 of the drape 11 during the manufacturing process. In the illustrated embodiment, the side pockets 20 are aligned and extend substantially the full length of the drape 11 between the patient edge 14 and the doctor edge 16.

An absorbent pad 24 attaches by either adhesive or stitching on the upper surface 12 of the drape 11. The absorbent pad 24 is preferably disposed generally centrally and coaxially along a longitudinal axis of the drape. The absorbent pad 24 is comprised of several layered absorbent fabric sheets.

The upper surface 12 further includes pockets 26 and 28 for receiving the examination and surgical instruments used during the procedure. The pockets 26 and 28 are positioned between the patient edge 14 and the absorbent pad 24 with their openings facing the patient edge 14. The pockets 26 and 28 have side edges and a bottom edge that are secured to the drape 11, whereby the instruments may be received into the pockets through an opening which faces the patient side edge 14, as best illustrated in FIG. 3.

Figure 3:
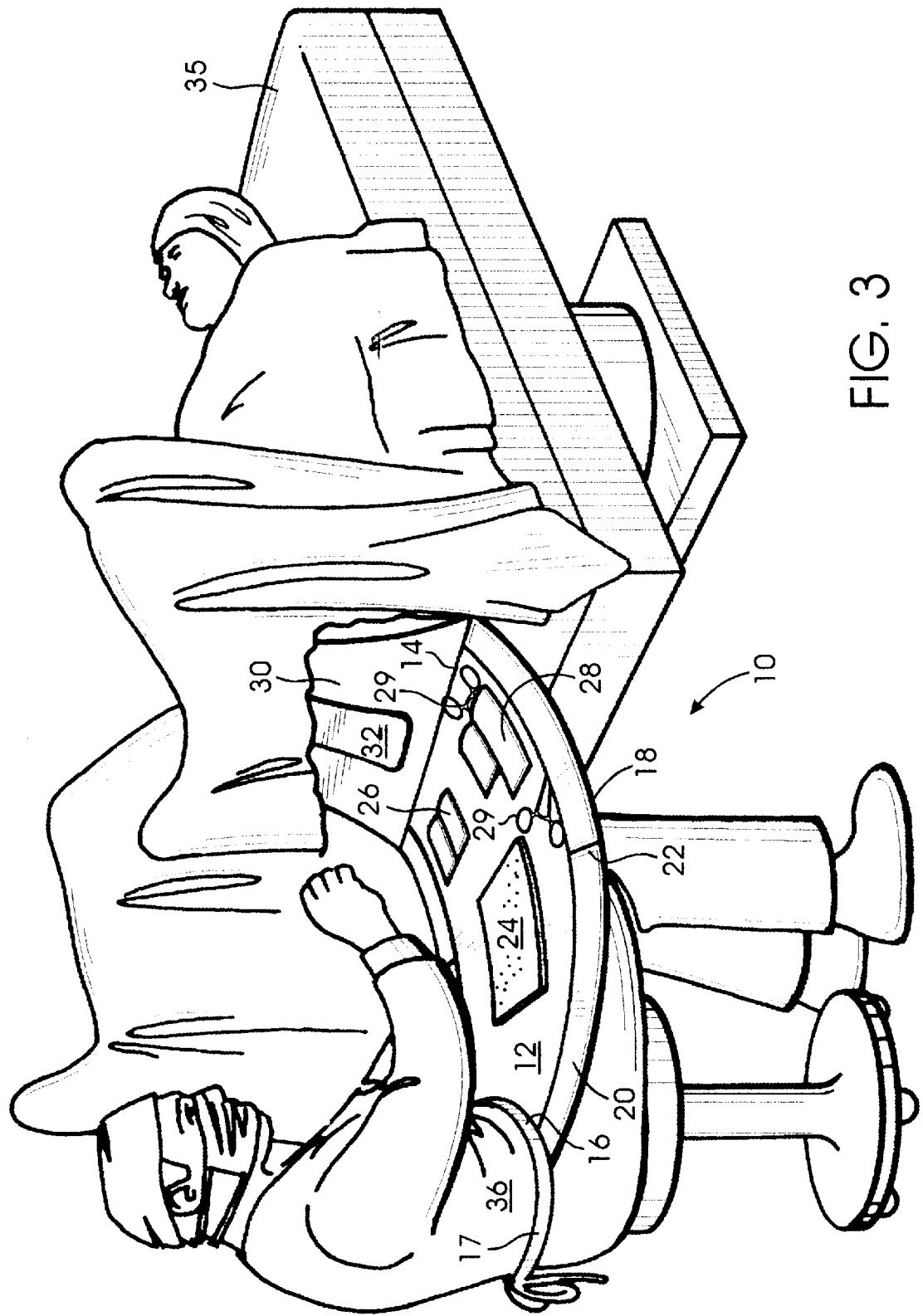
FIG. 3 is a perspective view of the perineal surgical apron of FIG. 1 in use during a surgical procedure.

FIG. 3 illustrates in perspective view the perineal surgical apron 10 attached to a patient lying in a lithotomy position on an operating table 35. The patient is covered by a patient covering 30, such as a conventional sheet-like drape or a lithotomy sheet with leggings produced by Kimberly-Clark. The doctor wears a protective medical garb 36. The doctor is seated between the legs of the patient. The patient edge 14 of the apron 10 is attached to the patient covering 30 by affixing the second side of the adhesive tape 15 to the patient covering 30. This is accomplished by removing a tear-away covering, exposing the adhesive layer, and pressing the exposed face of the adhesive tape 15 to the covering 30. The adhesive tape 15 is positioned on the patient covering below the fenestration site 32. The doctor edge 16 of the drape 11 is then attached to the doctor's medical garb 36. The adhesive surface of the tape 15' is exposed and pressed onto the doctor's medical garb 36. The free ends of the fabric strip 17 are then tied around the doctor's waist by the circulating nurse.

The drape 11 thereby defines a sheet-like operating surface between the patient and the doctor. The drape 11 defines a shallow U-shaped surface for receiving and holding instruments and fluids, and provides a surgical surface for the procedure. The doctor moves towards and away from the patient as necessary, without interfering with the surgical surface, and having access to the fenestration site 32 and the instruments 29. Surgical instruments 29 are stored in the instrument pockets 26 and 28 and are removed for use.

The absorbent pad 24, centrally disposed along the upper surface of the drape, facilitates use of the instruments 29 and the drape 11 during surgery. Excessive fluid released from the fenestration site can accumulate on the instruments 29. During the procedure, the instruments 29 are placed on the absorbent pad 24 for subsequent re-use during the procedure. The absorbent pad 24 removes some of the excess fluid from the instruments 29 when they are placed on the pad. Also, surgical instruments that fall from the doctor's hands are received in the U-shaped valley created by the drape 11 between the doctor and the patient. Instruments falling to the side of the drape 11 are received by the opposing side pockets 20 and thereby prevented from falling to the floor. This preserves the sterile environment and the instrument for subsequent use during the procedure. The size of the valley between the patient and the doctor may be adjusted by the doctor's movement, according to the comfort level of the doctor.

Figure 4:
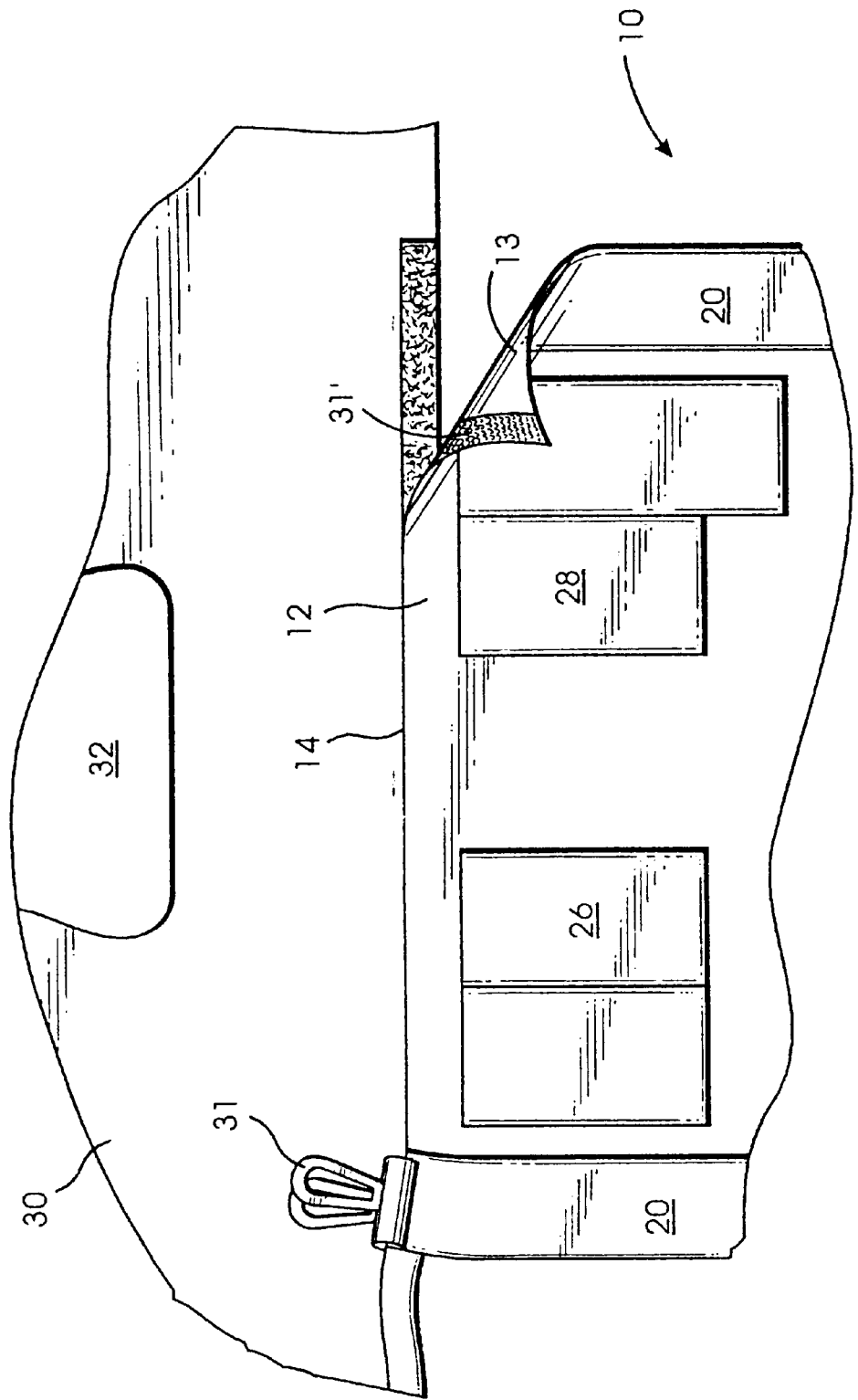
FIG. 4 is a cutaway top view of the perineal surgical apron of FIG. 1 illustrating attachment devices for securing the apron to a patient covering.

FIG. 4 illustrates an alternative embodiment of the perineal surgical apron 10, in which mating patches of hook and loop fasteners, such as VELCRO® brand strips 31 are used instead of adhesive tape along the lower surface 13 of the drape 11 for securing the apron to the patient and doctor. FIG. 4 also shows a second alternate embodiment having clips 33 that provide additional support between the drape 11 and the cover 30.

The present invention therefore provides perineal surgical aprons which create adjustable surgical work surfaces for doctors during gynecological or general surgical procedures. The aprons reduce doctor exposure to fluid and blood contact and eliminate the need for the doctor to turn or to stand in order to receive or replace surgical instruments from remote tables during such procedures. The apron also prevents a suture from being dragged across a surgeon's lap or knees and then becoming contaminated. Furthermore, the risk of breach of the sterile environment or the presence of excessive fluid and blood during a surgical procedure is reduced by pockets that receive dropped instruments and by absorbent padding centrally disposed on the surgical surface.

While the invention has been described in detail with particular references to the preferred embodiments thereof, it should be understood that many modifications and additions may be made thereto, in addition to those expressly recited, without departure from the spirit and scope of the invention as set forth in the following claims.

I claim:

1. A perineal surgical apron for defining a surgical operating surface during obstetric and surgical procedures performed, by a doctor wearing medical garb, on a patient wearing a covering and lying on an operating table, comprising:

a fluid impermeable drape having an upper surface and a lower surface and defining a patient edge and an opposing doctor edge, and two opposing side edges;

a pair of adhesive tapes, one of the pair attached to a respective one of the patient edge and the doctor edge;

an absorbent pad attached to a central portion of the upper surface of the drape and defining an area in the drape for absorbing fluids and blood from surgical instruments used during the surgical procedure;

at least two side pockets defined on a portion of the drape near each opposing side edge of the drape, each side pocket separated by a connector that attaches the pockets to the drape intermediate the patient edge and the doctor edge; and a plurality of open-ended instrument pockets attached to a portion of the drape near the patient edge for holding instruments for use during the surgical procedure, whereby, the drape being attached by the adhesive tapes to a covering on the patient and to a garb of the doctor, defines a working surface for the perineal surgical procedure.

2. The apron as recited in claim 1, wherein said absorbent pad comprises a plurality of layered absorbent fabric sheets.

3. The apron as recited in claim 1, wherein the side pockets are defined by folding a portion of the side of the drape over, whereby the upper surface of the portion faces the upper surface of the drape adjacent the portion; and wherein the connector comprises stitching that attaches the folded portion to the drape.

4. The apron as recited in claim 1, further comprising an elongate fabric strip attached to the doctor edge of the drape and having distal portions extending laterally from the opposing side edges, whereby the distal portions are tied together around a doctor for attaching the drape to the doctor for use of the drape during a perineal surgical procedure.

5. A perineal surgical apron for use in surgical procedures performed on a patient having a covering, and lying on an operating table, by a doctor wearing medical garb, comprising:

a fluid impermeable drape having an upper surface and a lower surface and defining a patient edge and an opposing doctor edge, and two opposing side edges;

first attaching means for connecting a lower surface of the patient edge of the drape to a covering on the patient;

second attaching means for connecting a lower surface of the doctor edge of the drape to a medical garb worn by a doctor; and a fluids-absorbent pad attached to a central portion of the drape upper surface and defining an area in the drape for absorbing fluid and blood from surgical instruments used during the surgical procedure, whereby the drape being attached to a covering on the patient and to a medical garb of the doctor, defines an sterile valley-shaped working surface for the perineal surgical procedure, which valley-shape varies depending on the position of the doctor relative to the patient.

6. The surgical apron as recited in claim 5, further comprising at least two side pockets defined within the sterile working surface at each opposing side edge of the drape, each side pocket separated by a connector that attaches the pocket to the drape intermediate the patient edge and the doctor edge.

7. The surgical apron as recited in claim 6, wherein the side pockets are defined by folding a portion of the side of the drape over, whereby the upper surface of the portion faces the upper surface of the drape adjacent the portion; and wherein the connector comprises stitching that attaches the folded portion to the drape.

8. The surgical apron as recited in claim 5, further comprising a plurality of open-ended instrument pockets attached to a portion of the upper surface of the drape near the patient edge for holding instruments for use during the surgical procedure.

9. The surgical apron as recited in claim 5, wherein said first attaching means and said second attaching means each comprise a double-sided adhesive tape, a first side of each of said tapes attaching said tape to said respective doctor and patient edges and a second side of each of said tapes attaching said drape to said covering and said medical garb.

10. The surgical apron as recited in claim 5, wherein said first attaching means comprises a first pad attached to the patient edge of the drape and a second pad attached to the covering on the patient, said first pad having a surface of a first character and said second pad having a surface of a second character for mating engagement with said first pad.

11. The surgical apron as recited in claim 5 further comprising attachment clips for securing the apron to the patient covering.

12. A perineal surgical apron for use in surgical procedures performed on a patient having a covering, and lying on an operating table, by a doctor wearing medical garb, comprising:

a fluid impermeable drape having an upper surface and a lower surface and defining a patient edge and an opposing doctor edge, and two opposing side edges;

first attaching means for connecting a lower surface of the patient edge of the drape to a covering on the patient;

second attaching means for connecting a lower surface of the doctor edge of the drape to a portion of a medical garb worn by a doctor; and at least two side pockets defined at each opposing side edge of the drape, each side pocket separated by a connector that attaches the pocket to the drape intermediate the patient edge and the doctor edge whereby, the drape being attached to the covering on the patient and to the doctor's medical garb, defines a sterile valley-shaped working surface for a perineal surgical procedure, said side pockets being defined within the sterile working surface.

13. The perineal surgical apron as recited in claim 12, further comprising a fluids-absorbent pad attached to a central portion of the drape upper surface and defining an area in the drape for absorbing fluid and blood from surgical instruments used during the surgical procedure.

14. The surgical apron as recited in claim 12, further comprising a plurality of open-ended instrument pockets attached to a portion of the upper surface of the drape near the patient edge for holding instruments for use during the surgical procedure.

15. The surgical apron as recited in claim 12, wherein the side pockets are defined by folding a portion of the side of the drape over, whereby the upper surface of the portion faces the upper surface of the drape adjacent the portion; and wherein the connector comprises stitching that attaches the folded portion to the drape.

16. The surgical apron as recited in claim 12, wherein said first attaching means and said second attaching means each comprise a double-sided adhesive tape, a first side of each of said tapes attaching said tape to said respective doctor and patient edges and a second side of each of said tapes attaching said drape to said covering and said medical garb.

17. The surgical apron as recited in claim 12, wherein said first attaching means comprises a first pad attached to the patient edge of the drape and a second pad attached to the covering on the patient, said first pad having a surface of a first character and said second pad having a surface of a second character for mating engagement with said first pad.

18. The surgical apron as recited in claim 12 further comprising attachment clips for securing the apron to the patient covering.

19. A perineal surgical apron for defining a surgical operating surface during perineal surgical procedures performed by a doctor wearing medical garb on a patient wearing a covering and lying on an operating table, comprising:

a fluid impermeable drape having an upper surface and a lower surface and defining a patient edge and an opposing doctor edge, and two opposing side edges;

a pair of adhesive tapes, one of the pair attached to a respective one of a lower surface of the patient edge and the doctor edge;

a fluids-absorbent pad attached to a portion of the drape upper surface and defining an area in the drape for absorbing fluid and blood from surgical instruments used during the surgical procedure; and at least two side pockets defined on at least one side edge by folding over a side portion of the drape whereby the upper surface of the side portion faces the upper surface of the drape adjacent the side portion and attaching together an intermediate section of the folded over side portion to the adjacent drape for separating said side pockets, whereby the side pockets each maintain the capability to receive articles during the surgery independent of a valley defined in the drape by the position of the doctor relative to the patient during the surgery, whereby the drape being attached by the adhesive tapes to a covering on the patient and to a garb of the doctor, defines a sterile valley-shaped working surface in the drape for the perineal surgical procedure, which valley-shape varies depending on the position of the doctor relative to the patient, and said side pockets being defined within the sterile working surface.

20. The perineal surgical apron as recited in claim 19, wherein the intermediate section is attached by stitching.

21. The perineal surgical apron as recited in claim 19, further comprising a plurality of open-ended instrument pockets attached to a portion of the upper surface of the drape near the patient edge.

22. The perineal surgical apron as recited in claim 19, wherein the pair of adhesive tapes comprise double-sided adhesive tapes whereby a first side of each of said tapes attaching said tape to said respective doctor and patient edges and a second side of each of said tapes for attaching said drape to said covering and said garb.

23. A perineal surgical apron for defining a surgical operating surface during perineal surgical procedures performed by a doctor wearing medical garb on a patient wearing a covering and lying on an operating table, comprising:

a fluid impermeable drape having an upper surface and a lower surface and defining a patient edge and an opposing doctor edge, and two opposing side edges;

a pair of adhesive tapes, one of the pair attached to a respective one of a lower surface of the patient edge and the doctor edge;

at least two side pockets defined on at least one side edge by folding over a side portion of the drape whereby the upper surface of the side portion faces the upper surface of the drape adjacent the side portion and attaching together an intermediate section of the folded over side portion to the adjacent drape for separating said side pockets, whereby the side pockets each maintain the capability to receive articles during the surgery independent of a valley defined in the drape by the position of the doctor relative to the patient during the surgery, whereby the drape being attached by the adhesive tapes to a covering on the patient and to a garb of the doctor, defines a sterile valley-shaped working surface in the drape for the perineal surgical procedure, which valley-shape varies depending on the position of the doctor relative to the patient, with said side pockets being defined within the sterile working surface.

24. The perineal surgical apron as recited in claim 23, further comprising a fluids-absorbent pad attached to a portion of the drape upper surface and defining an area in the drape for absorbing fluid and blood from surgical instruments used during the surgical procedure.

* * * * *